United States Patent
Hammer et al.

(10) Patent No.: US 12,300,376 B2
(45) Date of Patent: May 13, 2025

(54) CHARACTERIZING SOFT TISSUE STRESS FOR AMELIORATING INJURY IN PERFORMING A PROCESS

(71) Applicant: The Boeing Company, Chicago, IL (US)

(72) Inventors: Liisa Charlie Hammer, Seattle, WA (US); Karen C. Takatani, Renton, WA (US); Kevin F. Malik, Seattle, WA (US); Richard J. Gardner, Brier, WA (US); James D. Cotton, Issaquah, WA (US)

(73) Assignee: THE BOEING COMPANY, Arlington, VA (US)

( * ) Notice: Subject to any disclaimer, the term of this patent is extended or adjusted under 35 U.S.C. 154(b) by 47 days.

(21) Appl. No.: 17/453,586

(22) Filed: Nov. 4, 2021

(65) Prior Publication Data
US 2022/0230732 A1    Jul. 21, 2022

Related U.S. Application Data

(60) Provisional application No. 63/139,998, filed on Jan. 21, 2021.

(51) Int. Cl.
G16H 20/30    (2018.01)
G16H 30/20    (2018.01)
A61B 8/00     (2006.01)

(52) U.S. Cl.
CPC .............. *G16H 30/20* (2018.01); *A61B 8/485* (2013.01)

(58) Field of Classification Search
CPC ........ G16H 50/50; G16H 20/30; G16H 20/40; G16H 50/20; G16H 50/30; A61B 34/10; A61B 2034/105; A61B 5/4523
See application file for complete search history.

(56) References Cited

U.S. PATENT DOCUMENTS 9,610,036 B1    4/2017   De Sapio et al.
2003/0135129 A1 7/2003   Cusimano et al.
(Continued)

FOREIGN PATENT DOCUMENTS

EP    2839772 A1     2/2015
JP    2011141706 A   7/2011
(Continued)

OTHER PUBLICATIONS

Tse, Kwong Ming, et al. "A review of head injury and finite element head models." Am. J. Eng. Technol. Soc 1.5 (2014): 28-52. (Year: 2014).*

(Continued)

*Primary Examiner* — Jason B Dunham
*Assistant Examiner* — Constantine Siozopoulos
(74) *Attorney, Agent, or Firm* — MH2 Technology Law Group LLP

(57) ABSTRACT

Techniques for obtaining materials science properties of soft tissue for use in a damage model for ameliorating injuries in an individual performing a process are presented. The techniques can include obtaining physical parameters characterizing the soft tissue of the individual under each of a plurality of loading conditions, fitting a soft tissue damage model based on the parameters, and ameliorating injury in performing the process by implementing guidelines based on the soft tissue damage model.

20 Claims, 5 Drawing Sheets

(56) References Cited

U.S. PATENT DOCUMENTS

| | | | |
|---|---|---|---|
| 2017/0055836 | A1 | 3/2017 | Thelen et al. |
| 2021/0174929 | A1 | 6/2021 | Bruchal et al. |
| 2022/0192637 | A1* | 6/2022 | Kirby .................. A61B 8/485 |
| 2022/0338928 | A1 | 10/2022 | Hammer et al. |
| 2023/0067316 | A1 | 3/2023 | Hammer et al. |

FOREIGN PATENT DOCUMENTS

| | | | |
|---|---|---|---|
| WO | WO-2014201020 | A1 * | 12/2014 ............. A61B 8/085 |
| WO | 2021113725 | A1 | 6/2021 |

OTHER PUBLICATIONS

Golze, Doreen (PCT Authorized officer), Notification of Transmittal of the International Search Report and the Written Opinion of the International Searching Authority, or the Declaration, mailed Mar. 26, 2021, from related PCT Application No. PCT/US2020/063430, 15 pages.

Qasim et al., "Initiation and Progression of Mechanical Damage in the Intervertebral Disc Under Cyclic Loading Using Continuum Damage Mechanics Methodoloty: A Finite Element Study," Journal of Biomechanics 45 (2012) 1934-1940.

Extended European Search Report for European Application No. 21215965.1 dated Jun. 8, 2022 (11 pages).

De Sapio, V., et al., "Demographic Specific Musculoskeletal Models of Factory Worker Performance, Fatigue, and Injury," 2016 IEEE Aerospace Conference, IEEE, Mar. 5, 2016, pp. 1-13.

Lindner, Nora (PCT Authorized Officer), Notification Concerning Transmittal of International Preliminary Report on Patentability (Form PCT/IB/373) for International Application No. PCT/US2020/063430 dated Jun. 16, 2022 (8 pages).

Crisan, Carmen-Clara (PCT Authorized Officer), Notification of Transmittal of the International Search Report and the Written Opinion of the International Searching Authority, or the Declaration, mailed Jul. 19, 2022, for International Application No. PCT/US2022/022473, 22 pages.

Huber, G., et al., "Dependence of spinal segment mechanics on age and posture," Research Project F 2069 —Bundesanstalt für Arbeitsschutz und Arbeitsmedizin, May 3, 2010, pp. 1-173.

Qasim, M., et al., "Initiation and progression of mechanical damage in the intervertebral disc under cyclic loading using continuum damage mechanics methodology: A finite element study," Journal of Biomechanics, vol. 45, No. 11, Jul. 26, 2012 (Published online Jun. 8, 2012), pp. 1934-1940.

Weiss, J.A., et al., "Three-dimensional finite element modeling of ligaments: Technical aspects," Medical Engineering & Physics, vol. 27, No. 10, Aug. 8, 2005, pp. 845-861.

Zhang, Q., et al., "Techniques for In Vivo Measurement of Ligament and Tendon Strain: A Review," Annals of Biomedical Engineering, vol. 49, No. 1, Jan. 2021 (Published online Oct. 6, 2020), pp. 7-28.

Lake et al., "Effect of Fiber Distribution and Realignment on the Nonlinear and Inhomogeneous Mechanical Properties of Human Supraspinatus Tendon Under Longitudinal Tensile Loading," NIH Public Access Author Manuscript, J. Orthop Res. Dec. 2009; 27 (12), 1596, 17 pages.

Qasim et al., "Initiation and Progression of Mechanical Damage in the Intervertebral Disc Under Cyclic Loading Using Continuum Damage Mechanics Methodology: A Finite Element Study," Journal of Biomechanics 45 (2012) 1934-1940.

Rabello et al., "Substantiating the Use of Ultrasound Tissue Characterization in the Analysis of Tendon Structure: A Systematic Review," www.cjsportmed.com, vol. 31, No. 3, May 2021.

Schechtman et al., "In Vitro Fatigue of Human Tendons," J. Biometchanics, vol. 30, No. 8, pp. 829-839, 1997.

van Schie et al., "Ultrasonographic Tissue Characterisation of Human Achille Tendons: Quantification of Tendon Structure Through a Novel Non-Invasive Approach," Br. J. Sports Med, 2010, 44, 1153-1159.

Kim et al., "In Vivo Strain Analysis of the Intact Supraspinatus Tendon by Ultrasound Speckles Tracking Imaging," Journal of Othopaedic Research, Dec. 2011, 1931-1937.

Klauser et al., "Sonoelastography: Musculoskeletal Applications," Radiology: vol. 272, No. 3, Sep. 2014, 622-633.

Prado-Costa et al., "Ultrasound elastography: compression elastography and shear-wave elastography in the assessment of tendon injury," Insights into Imaging (2018) 9:791-814.

van Schie et al., "Efficacy of computerized discrimination between structure-related and non-structure-related echoes In ultrasonographic images for the quantitative evaluation of the structural integrity of superficial digital flexor tendons in horses," AJVR, vol. 62, No. 7, Jul. 2001, 1159-1166.

Doherty, F. (PCT Authorized Officer), Notification Concerning Transmittal of International Preliminary Report on Patentability and Written Opinion of the International Searching Authority mailed Nov. 9, 2023, for International Application No. PCT/US2022/022473, 15 pages.

Buckley, M.R., et al., "Validation of an Empirical Damage Model for Aging and In Vivo Injury of the Murine Patellar Tendon," Journal of Biomechanical Engineering, vol. 135, Apr. 2013, pp. 041005-1-041005-7.

Colombini, D., et al., "Preventing upper limb work-related musculoskeletal disorders (UL-WMSDS): New approaches in job (re)design and current trends in standardization," Applied Ergonomics, vol. 37, No. 4, Jul. 2006, pp. 441-450.

Fung, D.T., et al., "Subrupture Tendon Fatigue Damage," Journal of Orthopaedic Research, vol. 27, Feb. 2009 (Published online Aug. 6, 2008), pp. 264-273.

Takatani, K.C., et al., "A new approach to prevent overuse injuries of the rotator cuff supraspinatus tendon using the cumulative fatigue concept," Theoretical Issues in Ergonomics Science, vol. 18, No. 5, 2017 (Published online Jun. 22, 2017), pp. 455-476.

Van Eerd, D., et al., "Effectiveness of workplace interventions in the prevention of upper extremity musculoskeletal disorders and symptoms: an update of the evidence," Occup. Environ. Med., vol. 73, 2016 (Published Online First Nov. 9, 2015), pp. 62-70.

Office Action mailed in CA 3, 158,278 on Feb. 19, 2024. (5 Pages).

Office Action issued on Jun. 25, 2024, for Japanese Application No. 2022-534139, including English machine translation, 8 pages.

Garg, A., et al., "Applications of biomechanics for prevention of work-related musculoskeletal disorders," Ergonomics, vol. 52, No. 1, Jan. 2009, pp. 36-59.

Daneshmandi, H., et al., "An ergonomic intervention to relieve musculoskeletal symptoms of assembly line workers at an electronic parts manufacturer in Iran," Work, vol. 61, 2018, pp. 515-521.

Edwards, W. Brent, "Modeling Overuse Injuries in Sports as a Mechanical Fatigue Phenomenon," Exercise and Sport Science Reviews, vol. 46, No. 4, Oct. 2018, pp. 224-231.

Murakami, Y., et al., "Essential structure of S-N curve: Prediction of fatigue life and fatigue limit of defective materials and nature of scatter," International Journal of Fatigue, vol. 146, Article 106138, 2021 (Available online Jan. 5, 2021), 14 pages.

Pizzolato, C., et al., "Bioinspired Technologies to Connect Musculoskeletal Mechanobiology to the Person for Training and Rehabilitation," Frontiers in Computational Neruoscience, vol. 11, Article 96, Oct. 18, 2017, pp. 1-16.

* cited by examiner

CHARACTERIZING SOFT TISSUE STRESS FOR AMELIORATING INJURY IN PERFORMING A PROCESS

RELATED APPLICATION

This application claims priority to, and the benefit of, U.S. Provisional Patent Application No. 63/139,998, entitled, "Characterizing Soft Tissue Stress for Ameliorating Injury in Performing a Process", and filed Jan. 21, 2021, which is hereby incorporated by reference in its entirety.

FIELD

The subject matter described herein generally relates to ergonomics and industrial hygiene. More particularly, the subject matter disclosed herein relates to obtaining physical parameters used to develop guidelines for preventing or reducing soft tissue repetitive stress injuries.

BACKGROUND

Overuse injuries, particularly of the shoulder, including the supraspinatus tendon, are some of the most significant of ergonomics injuries. Accordingly, there is a need to understand the dynamics of workplace or other activities that contribute to and can result in stress, for example to a tendon, to address a task or repetition of tasks that contribute to an injury.

Existing ergonomic analysis and recommendations typically rely on theoretical constructs based on over-simplified characterizations of a shoulder joint complex. These can rely on psychophysical estimates of acceptable exertion levels or a generalization of the forces on the shoulder joint from a single moment load about a point. The existing approaches give only limited estimates of risk and are of limited use in practice.

Further, medical, therapeutic, and pharmacological research is dedicated to (or focuses on) individuals after injury has occurred: surgical procedures, physical therapy regimens, and treatments to speed recovery. Injury detection is focused on after a patient has self-reported an injury, not to screen for risk prior to injury. While traditional ergonomics practices seek to prevent injuries, it has only or so far been done so at the macro level with epidemiological methods: based on estimated work exposure, create an estimate of when a person will self-report an injury based on discomfort level or pain, and create guidelines below that threshold, and most injuries are defined by generalized body area: the entire shoulder, knee, or back, rather than individual components.

SUMMARY

This disclosure comprises examples according to the following Clauses.

Clause 1. A method of obtaining materials science properties of soft tissue for use in a damage model for ameliorating injuries in an individual performing a process, the method comprising: obtaining physical parameters characterizing the soft tissue of the individual under each of a plurality of loading conditions; fitting a soft tissue damage model based on the parameters; and ameliorating injury in performing the process by implementing guidelines based on the soft tissue damage model.

Clause 2. The method of Clause 1, wherein the obtaining the physical parameters comprises measuring at least one parameter of the soft tissue using an ultrasound device.

Clause 3. The method of any of Clauses 1 or 2, wherein the ultrasound device comprises a shear wave ultrasound device, and wherein the parameters comprise a shear modulus.

Clause 4. The method of any of Clauses 1, 2, or 3, wherein the ultrasound device comprises a longitudinal ultrasound device, and wherein the parameters comprise at least one of a Young's modulus or a cross-sectional area of the soft tissue.

Clause 5. The method of any of Clauses 1-4, wherein the plurality of loading conditions comprise a plurality of postures of the individual.

Clause 6. The method of any of Clauses 1-5, wherein the plurality of loading conditions comprise a plurality of positions of the individual.

Clause 7. The method of any of Clauses 1-6, wherein the soft tissue comprises a tendon, connective tissue, a vertebral disc, a ligament, or a muscle.

Clause 8. The method of any of Clauses 1-7, wherein the soft tissue damage model comprises a finite element method model characterizing the soft tissue.

Clause 9. The method of any of Clauses 1-8, wherein the soft tissue damage model comprises at least two damage regimes, each of the at least two damage regimes comprising one of: a no-damage regime, a sub-rupture damage regime, or a tear propagation regime.

Clause 10. The method of any of Clauses 1-9, wherein the guidelines based on the soft tissue damage model comprise a limitation on at least one of: a posture of the soft tissue, a number of repetitions of a movement of the soft tissue, a force applied to the soft tissue, a duration of maintaining a posture of the soft tissue, a duration of a repetition of a movement of the soft tissue, or a duration of a force applied to the soft tissue.

Clause 11. A system for obtaining materials science properties of soft tissue for use in a damage model for ameliorating injuries in an individual performing a process, the system comprising at least one electronic processor that executes instructions to perform operations comprising: obtaining physical parameters characterizing the soft tissue of the individual under each of a plurality of loading conditions; and fitting a soft tissue damage model based on the parameters; wherein implementing guidelines based on the soft tissue damage model ameliorates injury in performing the process.

Clause 12. The method of Clause 11, further comprising an ultrasound device, wherein the obtaining the physical parameters comprises measuring at least one parameter of the soft tissue using the ultrasound device.

Clause 13. The method of any of Clauses 11 or 12, wherein the ultrasound device comprises a shear wave ultrasound device, and wherein the parameters comprise a shear modulus.

Clause 14. The method of any of Clauses 11-13, wherein the ultrasound device comprises a longitudinal ultrasound device, and wherein the parameters comprise at least one of a Young's modulus or a cross-sectional area of the soft tissue.

Clause 15. The method of any of Clauses 11-14, wherein the plurality of loading conditions comprise a plurality of postures of the individual.

Clause 16. The method of any of Clauses 11-15, wherein the plurality of loading conditions comprise a plurality of positions of the individual.

Clause 17. The method of any of Clauses 11-16, wherein the soft tissue comprises a tendon, connective tissue, a vertebral disc, a ligament, or a muscle.

Clause 18. The method of any of Clauses 11-17, wherein the soft tissue damage model comprises a finite element method model characterizing the soft tissue.

Clause 19. The method of any of Clauses 11-18, wherein the soft tissue damage model comprises at least two damage regimes, each of the at least two damage regimes comprising one of: a no-damage regime, a sub-rupture damage regime, or a tear propagation regime.

Clause 20. The method of any of Clauses 11-19, wherein the guidelines based on the soft tissue damage model comprise a limitation on at least one of: a posture of the soft tissue, a number of repetitions of a movement of the soft tissue, a force applied to the soft tissue, a duration of maintaining a posture of the soft tissue, a duration of a repetition of a movement of the soft tissue, or a duration of a force applied to the soft tissue.

DRAWINGS

The above and/or other aspects and advantages will become more apparent and more readily appreciated from the following detailed description of examples, taken in conjunction with the accompanying drawings, in which.

Figure 4:
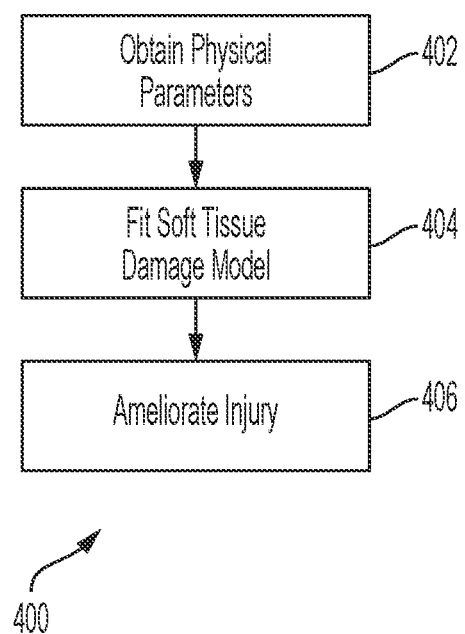
Figure 5:
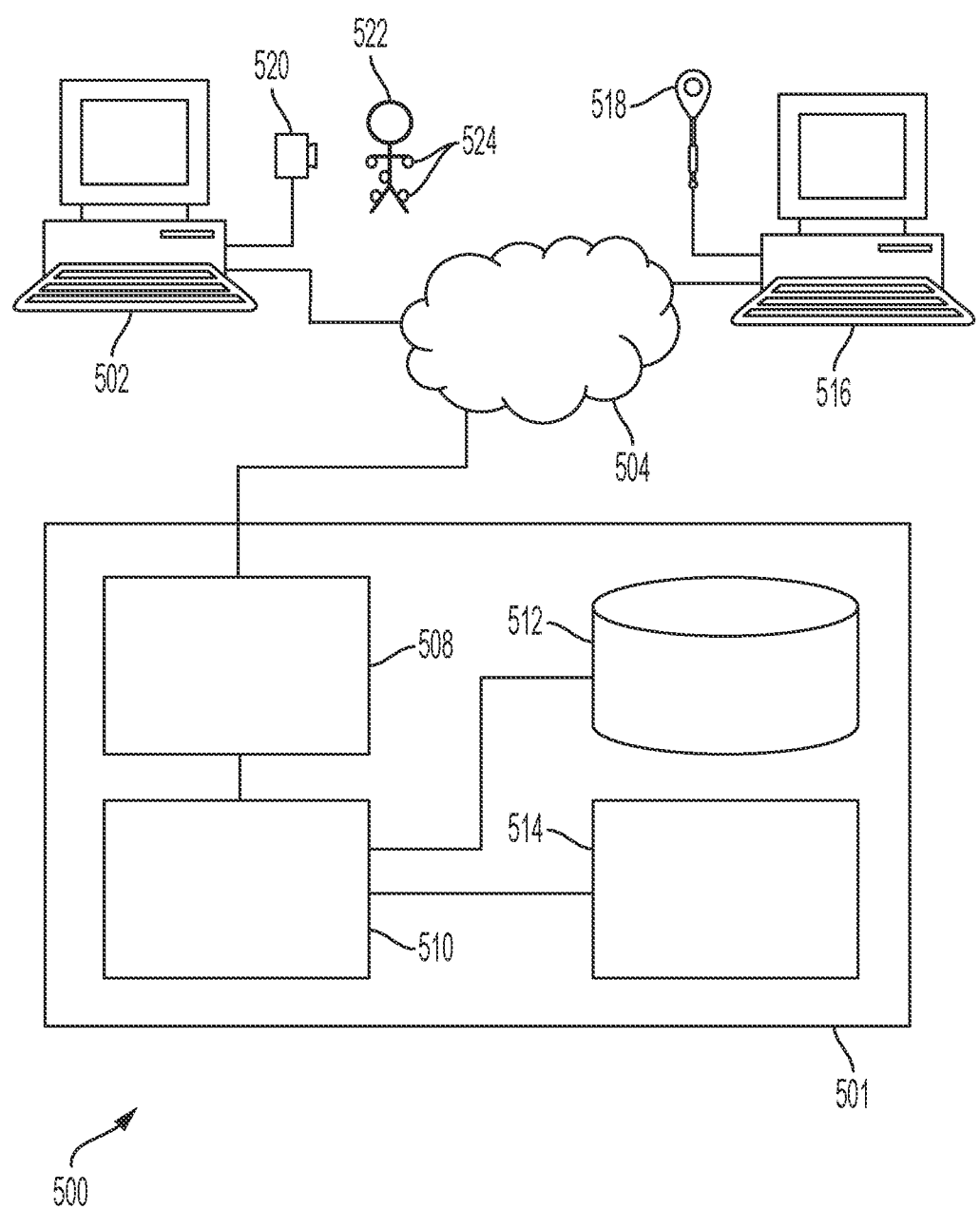

FIG. 4 is a flowchart depicting an example method of obtaining materials science properties of soft tissue for use in a damage model for ameliorating injuries in an individual performing a process according to various examples; and FIG. 5 is a schematic diagram of a system for obtaining materials science properties of soft tissue for use in a damage model for ameliorating injuries in an individual performing a process according to various examples.

DETAILED DESCRIPTION

Exemplary aspects will now be described more fully with reference to the accompanying drawings. Examples of the disclosure, however, can be embodied in many different forms and should not be construed as being limited to the examples set forth herein. Rather, these examples are provided so that this disclosure will be thorough and complete, and will fully convey the scope to those skilled in the art. In the drawings, some details may be simplified and/or may be drawn to facilitate understanding rather than to maintain strict structural accuracy, detail, and/or scale.

I. Introduction

The present disclosure relates to methods, systems, computer readable media for gathering information used to develop models for determining and predicting soft tissue damage. The models can apply principles of physics and chemistry related to the strength and resilience of human tissue in order to predict damage. For example, the models can apply materials science principles to human tissue based on novel criteria, such as dimensions (e.g., cross-sectional area of soft tissue), force (e.g., at different postures), stress distribution, resultant stress, and soft tissue performance parameters (e.g., healthy state, healing, accumulating damage, and damaged). Examples may utilize ultrasound and other techniques and devices to obtain empirical measurements of physical parameters used to fit the models. In some applications, the predictive models are used in addressing ergonomic issues related to a task to inform and establish guidelines to prevent or otherwise ameliorate potential for an injury.

Although some examples presented herein are disclosed in reference to shoulder injuries and the supraspinatus tendon, the methods and related aspects disclosed herein can also be applied to essentially any soft tissue, such as intervertebral (spinal) discs, ligaments, tendons, and tendon systems of interest and in biomimicry applications, such as in the design of artificial tendons. Further, essentially any tendon can be evaluated as part of the techniques disclosed herein. The tendon may include a mammalian tendon, such as a human tendon. Example tendons include: a teres minor tendon, an infraspinatus tendon, a supraspinatus tendon, a subscapularis tendon, a deltoid tendons, a biceps tendon, a triceps tendon, a brachioradialis tendon, a supinator tendon, a flexor carpi radialis tendon, a flexor carpi ulnaris tendon, an extensor carpi radialis tendon, an extensor carpi radialis brevis tendon, an iliopsoas tendon, an obturator internus tendon, an adductor longus tendon, an adductor brevis tendon, an adductor magnus tendon, a gluteus maximus tendon, a gluteus medius tendon, a quadriceps tendon, a patellar tendon, a hamstring tendon, a sartorius tendon, a gastrocnemius tendon, an Achilles tendon, a soleus tendon, a tibialis anterior tendon, a peroneus longus tendon, a flexor digitorum longus tendon, an interosseus tendon, a flexor digitorum profundus tendon, an abductor digiti minimi tendon, an opponens pollicis tendon, a flexor pollicis longus tendon, an extensor tendon, an abductor pollicis tendon, a flexor hallucis longus tendon, a flexor digitorum brevis tendon, a lumbrical tendon, an abductor hallucis tendon, a flexor digitorum longus tendon, an abductor digiti minimi tendon, an ocular tendon, a levator palpebrae tendon, a masseter tendon, a temporalis tendon, a trapezius tendon, a sternocleidomastoid tendon, a semispinalis capitis tendon, a splenius capitis tendon, a mylohyoid tendon, a thyrohyoid tendon, a sternohyoid tendon, a rectus abdominis tendon, an external oblique tendon, a transversus abdominis tendon, a latissimus dorsi tendon, an erector spinae tendon, and a combination thereof. Thus, examples may be used to develop models and generate injury amelioration guidelines for any activity, any soft tissue, involving any part of the body.

By way of further introduction, using the shoulder for performing work in a workplace is a challenge in extreme work environments. Shoulder mechanisms permit the placement, functioning, and control of the hand, the most useful part of the human body for manual labor or tool-intensive assembly. Hands, and therefore arms and shoulders, move to weld, paint, drill, cut, gut fish, or handle materials. The tool, hand, and shoulder system are often positioned overhead or in hard to reach places. The shoulder complex must support the weight of the arm, any tools being held to perform work, and force applied. Most manual work involving tools include tasks to be repeated many times during the course of a work period. Shoulder injuries are not limited to those incurred through work; they also often occur outside of the workplace, e.g., while at home and while participating in sports or other human activities.

A neutral shoulder posture is the upper arm straight and hanging alongside the body. Every time a shoulder is out of its neutral position, tendons are placed under tensile force, creating stress within the tendon. Each time the shoulder moves away from neutral position, force and repetition occur, exposing the tendon to cumulative fatigue damage. Note that the term "fatigue" is used throughout this disclosure in its mechanical sense—structural degradation from repeated forces—rather than physiological fatigue, which is the inability to perform activity because muscle contractile forces are reduced.

Studies linking shoulder pain or rotator cuff injuries to workplace factors have identified overhead work (defined as elbows above shoulders), applied force, repetitive motion, and physical loads as significant contributors. However, the quality of these studies varies, and evidence did not consistently demonstrate a significant dose—response relationship.

As a result, current published guidelines for shoulder-demand injury risk are insufficient for use in occupational ergonomics injury prevention programs. Existing guidelines are insufficient because they are based on previous workplace studies focused on self-reported pain and discomfort. They are further inadequate because they do not provide clear, acceptable limits for shoulder-based work activity in a workplace and they do not account for the interaction of posture, force and repetition, nor the interaction of posture, force, repetition, duration, and vibration. Instead, existing guidelines recommend reduction or elimination of overhead or extended shoulder postures. Practitioners are faced with degrees of unknown risk. Such unknown risk limits the solutions space for effective interventions.

While eliminating repetitive, awkward, or taxing shoulder use is infeasible in some industries, it could be ameliorated. Without sufficient risk thresholds, the question persists as to what degree these risk factors should be reduced to ameliorate or prevent injury. The question is further complicated because this type of work can involve many repetitive motions (e.g., painting) and/or forces (e.g., drilling) and/or loads (e.g., welding). Guidelines may therefore take into account risk factor interaction and work/rest cycles.

Given the inability of establishing causality with epidemiological data alone, an alternative approach is needed. The models and related aspects disclosed herein bridge many of the gaps that traditional epidemiological studies have not been able to close and instead use a fatigue model of cumulative damage to predict and prevent injuries in certain aspects.

This is a new approach to model and characterize stress on musculoskeletal soft tissue (e.g., connective tissue, shoulder tendon, vertebral discs, ligaments, muscles, etc.) subjected to different stimuli and conditions, thereby demonstrating soft tissue fatigue failure properties. The results of the model can be used to characterize postures that are "good," "bad," and "worse" during use while working or during other daily activities (e.g., hobbies, sports). Using the model involves gathering and interpreting physical parameters (e.g., Young's modulus, shear modulus, strain, cross-sectional area of the tissue) subject to different stimuli and conditions in vivo. The model is premised on materials sciences methodology.

The soft tissue material fatigue model may be implemented as a finite element representation of soft tissue (e.g., tendon) material behavior. Fidelity of the model is anticipated by incorporating nonlinear behavior and addition of complex loading and vibration/fatigue cycling of the soft tissue. It has been found that this results in a combined effect leading to injury with definite multipliers, which was previously not known or understood in the field of ergonomics.

The results of the modeling allows for determination of criteria that can be used to develop guidelines to structure activities in a way so that subjects are not exposed to overuse that could otherwise result in injury, if not ameliorated. The models can be used to set exposure limits and create usable work/rest cycles to predict and prevent overuse injuries, leading to a significant change in current approaches to ameliorating and reducing injuries. This allows for analysis and end results that were not previously done (and could not be done with existing knowledge or models). Examples disclosed herein are advantageous for heavy industry, especially where overhead work, repetition, and force exist, and for sports. Examples can be used to redesign work practices exceeding reasonable tendon strain or stress thresholds, create work-rest cycles based on collagen damage and repair rates, identify individuals for whom the model is not conservative, and implement strength training to improve tendon material properties.

In sum, there is a need to analyze and determine what factors lead to musculoskeletal soft tissue injuries. In particular, there is a need to determine parameters that are used to develop the damage models disclosed here. Such parameters include, for example, one or more of Young's modulus, shear modulus, strain, and cross-sectional area of the soft tissue. As described in detail herein, ultrasonic interrogation can estimate material acoustic properties of biological material within a living subject, and these can be correlated with certain mechanical properties, such as Young's modulus. These and other techniques are described in detail below.

II. Exemplary Methods

Figure 1:
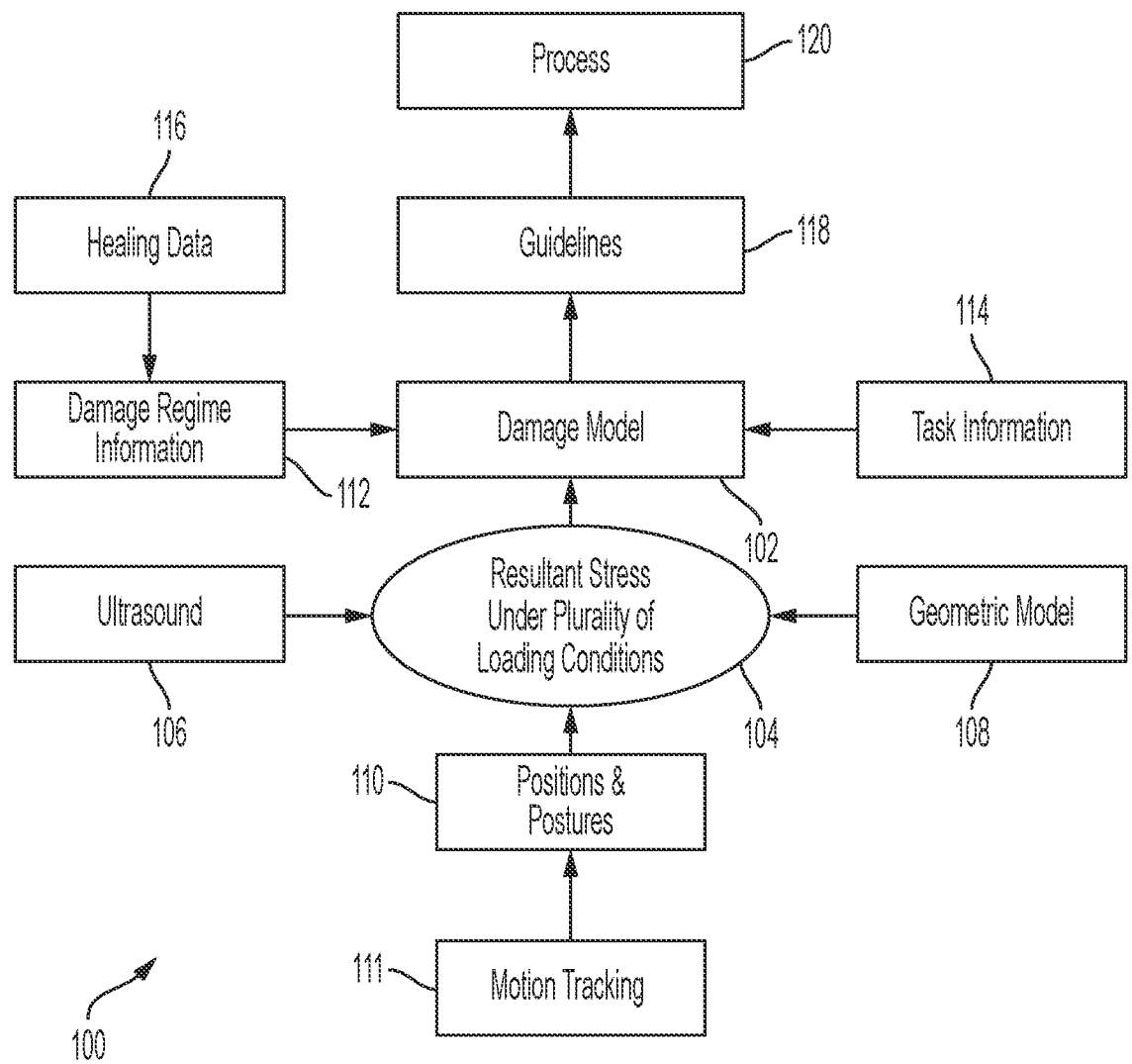
FIG. 1 is a schematic hybrid diagram that depicts example system elements and method steps according to various examples.

FIG. 1 is a schematic hybrid diagram 100 that depicts example system elements and method steps according to various examples. Central to diagram 100 is damage model 102.

A. Damage Model & Damage Regimes

Model 102 may account for one or more of the following sequential soft tissue damage regimes: (1) no damage; (2) subrupture damage accumulation (micro-tears); (3) damage accumulation in the form of a growing tear or fissure, cellular matrix damage or other biological damage; and (4) a state of catastrophic failure or separation of the tendon structure. Model 102 may determine when to transition from one damage regime in the sequence to the next.

To that end, model 102 uses damage regime information 112. Damage regime information 112 can be in the form of computer files, e.g., in tab-delimited or comma-separated value (CSV) format. Damage regime information 112 can be obtained during use of an example by being read from persistent electronic storage by a computer, or by the data being entered into file format and stored in the computer, by way of non-limiting examples.

Damage regime information 112 may be produced based on empirical measurements of materials science properties of soft tissue, e.g., based on ultrasound data, computerized axial tomography (CAT) scan data, magnetic resonance imaging (MRI) scan data, destructive testing data, cadaver material, animal material, polymer surrogate material, molecular dynamic modeling (MDM) data, publication data, or a combination thereof.

Damage regime information 112 may be in the form of separate sets of damage regime information for each damage regime. Each set of damage regime information can quantify a number of repetitions at a given stress for the soft tissue to transition out of the respective damage regime. For example, the first information can quantify a number of repetitions per given stress for the soft tissue to transition out of the first damage regime; the second information can quantify a number of repetitions per given stress for the soft tissue to transition out of the second damage regime, and, for examples that include a third damage regime, the third information can quantify a number of repetitions per given stress for the soft tissue to transition out of the third damage regime.

Each damage regime information can be in the form of a curve quantifying a number of repetitions at a given stress for the soft tissue to transition out of the respective damage regime, e.g., with stress as an independent variable and repetitions as a dependent variable. For example, each information can be in the form of an S-N curve according to various examples. When stored in a computer, such information can be in the form of a set of ordered pairs (S, N), where S represents stress and N represents a number of repetitions to transition out of the respective regime.

According to various examples, the first damage regime can be a no-damage regime, the second damage regime can be a sub-rupture damage regime, and, for examples that include it, the third damage regime can be a tear propagation regime. (Note that any combination of at least two damage regimes can be used according to various examples, not limited to those explicitly set forth presently.) The no-damage regime can represent a situation in which micro-damage (e.g., sub-ruptures) occur in the soft tissue at substantially the same rate as they are healed. Transition out of the no-damage regime can represent sub-rupture accumulation at a rate faster than the healing rate for the respective soft tissue. The sub-rupture regime can represent a situation where the micro-damage (e.g., sub-rupture damage) accumulates, but no macroscopic tear has yet formed. Transition out of the sub-rupture regime can represent that a macroscopic tear has formed. The tear propagation regime can represent a situation where a tear has formed and is propagating through the soft tissue. Transition out of the tear propagation regime can represent that the soft tissue has fully ruptured.

Note that examples that incorporate either or both of the no-damage regime and the sub-rupture regime can predict damage to subject soft tissue prior to the subject realizing that damage has occurred. For example, soft tissue within these regimes can be damaged, but cause no pain or discomfort to the subject.

Note that while soft tissue such as tendons behave like materials with predictable fatigue failure at given stress levels and cycles, they are also able to self-repair. When people are engaged in physical activity, the effects of repeated stress on soft tissues result in small fissures, referred to herein as microtrauma or subruptures. Subruptures themselves are not harmful to the body because the body will repair itself to become stronger given a sufficient recovery period; this is the underlying benefit of exercise. With insufficient recovery period, the tendon becomes damaged and eventually an injury will occur. Thus, model 102 may take into account rest periods in which the soft tissue self-repairs. Accordingly, damage regime information 112 is also based on healing data 116. Healing data 116 may include data representing healing rates of various soft tissues. For example, healing data 116 may include healing rates of each of a variety of tendons. Further, healing data 116 may be arranged according to demographic information. For example, healing data may include healing rates of the supraspinatus tendon according to various age groups, e.g., 18-30, 30-40, 40-50, and 50-60 years old.

Damage model 102 may determine whether damage has occurred, or predict that damage will occur, by evaluating task information 114 in light of its damage estimations and predictions. Task information 114 can be in the form of computer files, e.g., in tab-delimited or comma-separated value (CSV) format. Task information 114 can be obtained by being read from persistent electronic storage by a computer, or by the data being entered into file format and stored in the computer, by way of non-limiting examples.

Task information 114 can represent the exposure that a subject might accrue (or has accrued) over the course of completing one task that forms part of an overall process, e.g., a manufacturing process. The exposure can be in the form of a number of repetitions, an associated time interval in which the repetitions are performed, and a description of a movement for each repetition, e.g., in narrative form. According to some examples, task information 114 can account for multiple types of movements.

In order to evaluate task information 114 in light of the damage estimations and predictions of model 102, the resultant stress 104 of each repetition under a plurality of loading conditions may be determined. This data may be combined with task information 114 and damage regime information 112 to determine cumulative damage over the course of the task, as described in detail below.

B. Resultant Stress

To determine whether soft tissue damage has or will occur, damage model 102 uses task information 114, which indicates the repetitive injury exposure that the subject has (or will) incurred in performing a task, as compared to damage regime information 112. To do so, damage model 102 first determines resultant stress 104 for each movement represented in task information 114. Then, based on resultant stress 104 and task information 114, and using damage regime information 112, model 102 determines whether the soft tissue has (or will) transition into a different damage regime.

Resultant stress 104 may be determined by first determining resultant force. The term "resultant force" refers to a combination of the forces acting on soft tissue during work, including posture, position, vibration, tool weight, force vector applied at the hand, arm weight, etc. Tensile force is relevant to shoulders, but other soft tissue, such as intervertebral discs, can experience compressive force. Other types of soft tissue can experience both compressive and tensile forces. The force can be determined by observation and empirical measurements, as described in detail below, or by using an estimation and/or modeling technique, such as finite element modeling (FEM) and/or electromyography (EMG). The force can be express in Newtons, and the stress can be expressed in Megapascals (MPa), for example.

Stress will increase at certain postures and under certain loading conditions. There will be certain muscle/tendon structures having a relationship or correlation between the tissues that participate in the tasks. Therefore, stress may be determined at a number of different loading conditions (e.g., posture and/or positions). Posture and position are described presently in reference to FIGS. 2 and 3.

Figure 2:
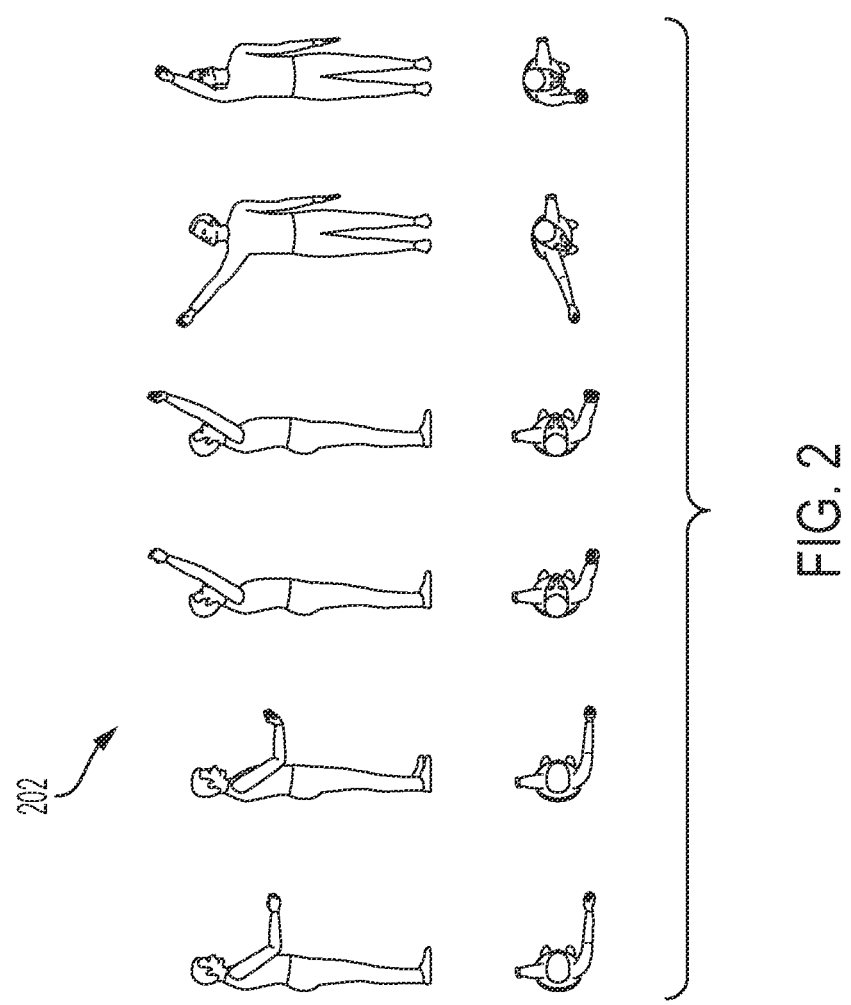
FIG. 2 is a schematic diagram depicting various postures according to various examples.

FIG. 2 is a schematic diagram depicting various postures 202 according to various examples. "Posture" can refer to qualitative characterizations of the subject's body or part thereof. A posture can be defined in terms of relative positions of identified landmarks. For example, a particular posture referred to as "overhead work" can be defined as the situation when the subject's elbow is above the subject's shoulder. In general, a posture can define a body position in a qualitative way, such that it can be observed and compared to another observation or position. A position of a subject (or a portion of the subject's body) can be determined by observational study by an ergonomist or industrial engineer according to various examples.

Figure 3:
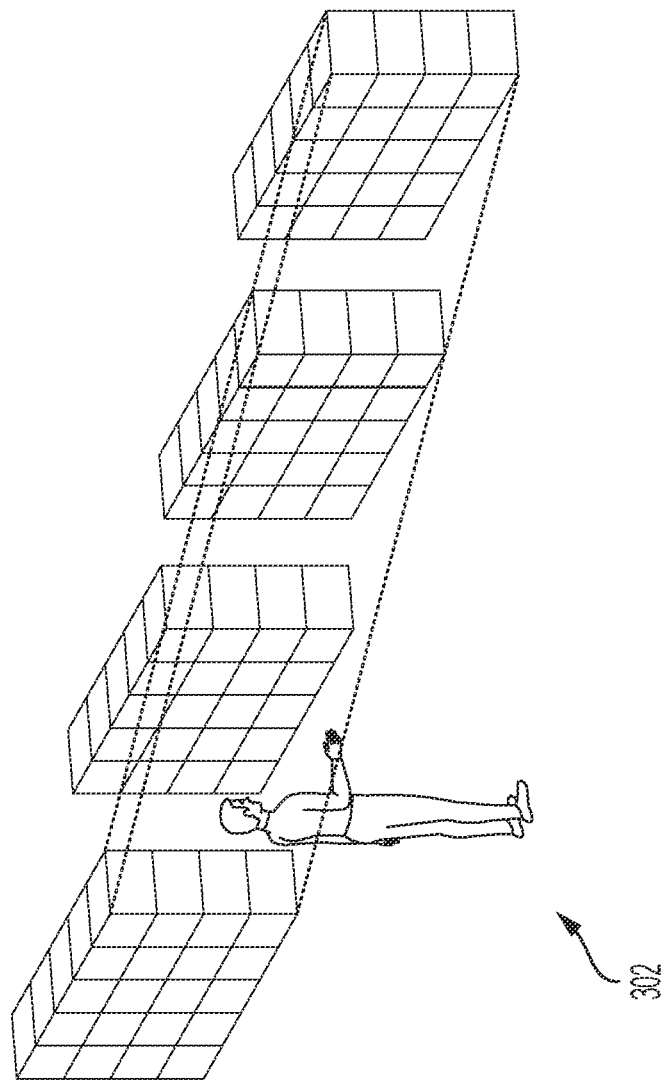
FIG. 3 is a schematic diagram illustrating various positions according to various examples.

FIG. 3 is a schematic diagram illustrating various positions 302 according to various examples. Here, "position" can refer to quantitative characterization of the subject's body or part thereof. For example, a position can be defined using measurement equipment, with units like length, angle, or x-y-z coordinates. For example, a tendon position can be defined at coordinates (0 cm, 5 cm, 1 cm), where origin (0 cm, 0 cm, 0 cm) is where the tendon attaches to the humerus, and the coordinates correspond to positions in the following planes as follows: x=saggital, y=transverse, and z=coronal. As shown in FIG. 3, for example, a number of virtual pigeonholes distributed throughout three-dimensional space about (e.g., encompassing) the subject may define a plurality of positions of a subject's arm and hand.

Both position and posture of a subject (or a portion of the subject's body) can be determined through the use of motion tracking 111 according to various examples. Such motion tracking 111 may be performed by a motion tracking system that uses optical (e.g., infrared), sonic (e.g., ultrasonic), or radio-frequency (RF) transmitters or reflectors and corresponding sensors to continuously track the subject's limb or other body portion in three-dimensional space. Such sensors may be distributed in three-dimensions about a space in which the subject is positioned, and the transmitters/reflectors may be attached to the subject; this description represents "outside-in tracking. Alternately, according to some examples, the motion tracking system may utilize "inside out" tracking, in which the sensors are placed on the subject, and the transmitters/reflectors are distributed about the space. Some examples utilize motion tracking that does not include transmitters or reflectors. Such examples may track motion using one or more video cameras and, for example, computer vision analysis. Regardless as to the type, the motion tracking system may determine posture by matching determined locations of the subject's body or part thereof to data associated with various positions. The motion tracking system may determine positions by specifically measuring distances in relation to the subject's movements.

Returning to the description of FIG. 1, the resultant stress 104 of a single repetition may be determined by dividing the resultant force for the repetition by the area of the affected soft tissue cross-sectional. Thus, determining resultant stress 104 may include determining the cross-sectional area of the affected soft tissue. Examples may determine such an area using a variety of techniques.

Some examples determine the cross-sectional area of the affected soft tissue based on a geometric model 108. Such a model may approximate the shape of the cross-sectional area as a circle, an oval, or a different two-dimensional geometric shape. The geometric model 108 may be based on past research as to the shape of various soft tissue cross-sections. Further, the geometric model 108 may account for age, gender, size, and other particular demographics of the subject based on past empirical measurements performed on individuals with similar characteristics. Thus, the soft tissue cross-sectional area for the geometric model 108 can be based on average cross-sectional areas for various soft tissue types, specific cross-sectional areas per demographic combination (e.g., sex, age, gender, height, weights, etc.), or a combination of such data.

Some examples determine the cross-sectional area of the affected soft tissue through the use of ultrasound 106. For example, longitudinal ultrasound using a longitudinal ultrasound device may be used to directly measure the dimensions of the cross-sectional area. Alternately, or in addition, longitudinal ultrasound may be used to measure Young's modulus for the soft tissue. The stress may then be computed from the measured Young's modulus. Whether cross-sectional area or Young's modulus, the measurements may be performed for a variety of positions and postures 110. This assists in more accurate estimates of stress, as soft tissue such as tendons typically has changing properties as position changes, e.g., as tendons elongate, they tend to become stiffer.

Alternately, or in addition, according to some examples, shear wave ultrasound using a shear wave ultrasound device may be used. For example, shear wave ultrasound may be used to measure a shear modulus. The stress may then be computed from the measured shear modulus. Again, these measurements may be computed for a variety of positions and postures 110.

C. Predicting Damage and Generating Guidelines

Based on the resultant stress 104, the damage model 102 can determine whether damage has or will occur. The determination can utilize material science properties of the soft tissue. According to some examples, the determination can be performed as follows. For convenience of exposition, the determination is described in terms of prediction; however, the determination may be equally used to detect damage already incurred. First, the resultant stress 104 can be determined as described above. In particular, the resultant stress 104 per repetition (and/or per repetition) may be determined. Second, the cumulative resultant stress can be computed by multiplying the resultant stress 104 for a particular repetition by the number of repetitions performed or to be performed, as represented in the task information 114. Third, the cumulative resultant stress is compared to the damage regime information 112 as informed by the healing data 116. For example, for a cumulative stress that represents R repetitions each at a stress level of S, the cumulative stress $\Sigma S$ can be considered an independent variable in the information representing the current damage regime of the soft tissue, and the corresponding dependent variable R' in terms of a number of repetitions for transition out of the damage regime can be identified. Fourth, the number of repetitions R' of the identified dependent variable is compared with the number R of repetitions set forth in the task information 114. If the former is greater than the latter, then the soft tissue is predicted to remain in its current damage regime, and therefore no additional damage is predicted. If, however, the former is less than or equal to the latter, then the soft tissue is predicted to transition out of the respective damage regime. In that case, the soft tissue is predicted to undergo damage. Thus, the soft tissue is predicted to undergo damage when the number of repetitions R set forth in the task information 114 for stress level S meets or exceeds the number of repetitions R' corresponding to S per the information characterizing the current damage regime for transition out of the current damage regime as set forth in the damage regime information 112 as informed by the healing data 116.

This process can include multiple tasks as represented in the task information 114. For example, the products of the repetitions and stress levels can be summed. This sum can be compared to the damage regime information 112. If the sum is greater, then the soft tissue is predicted to undergo damage, that is, transition damage regimes. Otherwise, the soft tissue is predicted to remain in the current damage regime.

An example usage of model 102 to predict damage (or ascertain if damage has already occurred) is set forth presently. Per this example, the task information 114 includes:
Task A Repetitions: 50
Task B Repetitions: 500
Task C Repetitions: 5000

The resultant force for repetitions of each task may be set forth in the task information 114 or determined as part of computing the resultant stress 104 as:
Task A Force: 150N
Task B Force: 100N
Task C Force: 50N Stress is force divided by cross-sectional area of the tendon, which may be determined from ultrasound 106 and/or a geometric model 108. For purposes of this example, the cross-sectional area is 50 mm$^2$. Thus, Task A Stress=3 MPa, Task B Stress=2 MPa, and Task C Stress=1 Mpa per repetition. Per this example, the damage regime information may indicate a transition out of the no-damage regime occurs at 1000 cycles at 4 MPa (this is one point along the curve).

The stress from the tasks may be compared to the no-damage regime limit as 3 MPa*50+2 MPA*500+1 MPa*5000>4 MPa*1000. This means that the no-damage regime is exceeded. Thus, the next regime (e.g., subrupture) would need to be calculated to and maybe the next one after, and so on up to the fracture regime. Note that healing data 116 may also be applied if multiple tasks are combined with rest periods in between (e.g., a percentage reduction in exposures, moving to a lower point on the curve, etc.).

The calculations presented above in this illustration provide a point solution (just one number and one answer) for one iteration. For better model fidelity, this iteration can be run a number of times, sampling from distributions of, for example, soft tissue geometries, the force on the soft tissue, and potentially variation in the repetitions. For example, this can be a model run multiple times with slightly different probabilistic inputs, similar to a Monte Carlo simulation. This provides an output of the risk with some boundaries or bands around it (e.g., a 95% confidence interval, etc.). Optionally, other variables, such as demographics are also added to the model.

Based on the damage model, examples can produce guidelines 118 for avoiding or ameliorating soft tissue damage. As used herein, the term "guideline" embraces a recommended set of evidence-based limits on one or more of force (e.g., vibration, tool weight, force vector applied at the hand, arm weight, etc.), posture, position, frequency, duration and/or recovery, intended to safeguard human tissue material from the risk of injury due to tendon damage during human activity such a manufacturing or other processes. In general, each guideline can reduce a number of repetitions and/or an amount of stress corresponding to actions in the task information 114. Each guideline may thus specify a posture or position of the soft tissue, a number of repetitions of a given movement of the soft tissue, a force applied to the soft tissue, a duration of maintaining a given posture or position of the soft tissue, a duration of a repetition of a given movement of the soft tissue, a duration of a given force applied to the soft tissue, or a combination thereof. Such parameters can be specified such that the calculations described above predict no damage. The parameters so specified can form all or part of a guideline.

In general, the guideline can reduce the stress on the soft tissue by reducing the force on the soft tissue in any of a number of ways. The force on the soft tissue can be a resultant force on the soft tissue, the force being the result of posture (or position), weight (e.g., of the arm and/or holding an object such as a tool), applied force vector (e.g., pushing at the hand), vibration (from holding a vibrating object such as a hand tool), etc. According to some examples, the force is reduced by placing a limitation on any of the above parameters.

The force on the soft tissue can alternately, or in addition, be reduced placing a limitation on the position and/or posture of the subject's body or portion thereof, thus affecting a position and/or posture of the soft tissue. According to various examples, the guideline can include a limitation on at least one of a position of the soft tissue, and/or a posture of the soft tissue.

Alternately, or in addition, the force on the soft tissue can be reduced placing a limitation on a temporal duration of a movement, position, or posture. That is, the guideline can place a limitation on any, or a combination, of: a duration of maintaining a given posture of the soft tissue, a duration of maintaining a given position of the soft tissue, a duration of a repetition of a given movement of the soft tissue, and/or a duration of a given force applied to the soft tissue.

According to some examples, the guidelines can include imposed rest periods. Such examples can utilize a representation of the healing processes that counteract micro-damage or macro-damage. The rest periods can represent sufficient time for such healing processes to counteract any accumulated damage.

Once produced, the guidelines can be output and utilized in a process, such as a manufacturing process. The guidelines can be output in any of a variety of forms. According to some examples, the guidelines are output in narrative form using pre-generated narrative templates. For example, if the computations indicate that the number of repetitions should be reduced from 1000 to 725, the guideline can populate these numbers into a template that reads in part, "The number of repetitions for action X should be reduced from Y to Z," where X, is replaced with a description of the action, Y is replaced by 1000, and Z is replaced by 725. The formatted guidelines can be output by displaying on a computer monitor, by email, or by any other techniques that provide the information to a person or process.

Implementing the guidelines in a process can include providing the guidelines to workers on an assembly line, for examples in which the process is a manufacturing process. The workers can then alter their tasks accordingly. For examples in which the process is an athletic training process, the guidelines can be provided to the trainer, who alters the athlete's training plan accordingly. Further, the guidelines can be used to design production systems, products, work tasks, training plans, etc.

FIG. 4 is a flowchart depicting an example method 400 of obtaining materials science properties of soft tissue for use in a damage model for ameliorating injuries in an individual performing a process according to various examples. Method 400 can utilize material science properties of soft tissue to reduce the potential for injuries to those performing a process. For example, each worker can have one or more tasks that form part of the manufacturing process, e.g., on an assembly line. The tasks for each worker can be modified by the one or more guidelines produced by method 400. Alternately, method 400 can be used to ameliorate repetitive stress injuries of an athlete executing a training program, for example. The athlete can have one or more exercises that form part of the training program. The exercises can be modified by the one or more guidelines produced by method 400. In general, method 400 can be practiced to ameliorate repetitive stress injuries in any type of process that includes repetitive movements by a person, not limited to manufacturing or athletic processes.

Method 400 can be used to ameliorate injuries to any of a variety of soft tissues. According to some examples, method 400 can be used to ameliorate injuries to tendons or tendon complexes. Examples of such tendons and tendon complexes are presented above in reference to FIGS. 1-3. Alternately, method 400 can be used to ameliorate injuries to connective tissue or musculoskeletal soft tissue. In general, non-limiting examples of soft tissues for which examples can be implemented include tendons, tendon complexes, intervertebral (spinal) discs, and ligaments.

Method 400 may be implemented using system 500 as shown and described below in reference to FIG. 5. Method 400 includes extra-computer actions that provide improvements in the field of industrial hygiene. Such actions include, for example, obtaining physical parameters using, for example, ultrasound and/or motion detection devices.

At 402, method 400 obtains physical parameters characterizing soft tissue of an individual under each of a plurality of loading conditions. The physical parameters can include soft tissue dimensions, such as cross-sectional area, Young's modulus, and/or shear modulus. The physical parameters may be obtained using an ultrasound device, such as a longitudinal or shear wave ultrasound device, e.g., as described above in reference to FIG. 1. The physical parameters may be obtained using a motion tracking system, e.g., as described above in reference to FIG. 1. The physical parameters may be obtained for a plurality of loading conditions, e.g., a variety of positions and/or postures. Essentially any physical parameter that contributes to determining a resultant stress, e.g., as shown and described above in reference to resultant stress 104 of FIG. 1, may be obtained.

At 404, method 400 fits a soft tissue damage model based on the physical parameters of 402. Fitting the model may include adapting a model to the physical parameters of 402. The soft tissue damage model may be based on a Finite Element Method (FEM) simulation of the soft tissue. The soft tissue damage model may account for at least two damage regimes, e.g., at least two of a no-damage regime, a subrupture regime, and a tear propagation regime, as shown and described above in reference to FIG. 1.

At 406, method 400 ameliorates injury in a subject performing the process under consideration. To do so, method 400 may include developing guidelines and implementing the guidelines in the process. The guidelines can include a limitation on at least one of: a posture of the soft tissue, a number of repetitions of a given movement of the soft tissue, a force applied to the soft tissue, a duration of maintaining a given posture of the soft tissue, a duration of a repetition of a given movement of the soft tissue, or a duration of a given force applied to the soft tissue, as shown and described above in reference to FIG. 1. The guidelines may be implemented by providing the guidelines to workers on an assembly line, for example. Consequently, by following the guidelines, the risk of soft tissue injury to the subject due to repetitive stress injury is ameliorated.

III. Exemplary Systems and Computer Readable Media

FIG. 5 is a schematic diagram of a system 500 for obtaining materials science properties of soft tissue for use in a damage model for ameliorating injuries in an individual performing a process according to various examples. For example, FIG. 5 illustrates various hardware, software, and other resources that can be used in implementations of method 400 according to disclosed examples.

In examples as shown, system 500 includes computer 501, ultrasound device 516 (including ultrasound transducer 518) and motion tracking device 502 (including sensors 520, e.g., cameras, and transmitters or reflectors 524, which are attached to a body of subject 522). Ultrasound device 516 may be a shear wave ultrasound device or a longitudinal ultrasound device, for example. Computer 501 can be incorporated in one or more servers, clusters, or other computers or hardware resources, or can be implemented using cloud-based resources. Computer 501 includes volatile memory 514 and persistent memory 512, the latter of which can store computer-readable instructions, that, when executed by electronic processor 510, configure computer 501 to at least partially perform methods, e.g., method 400, as shown and described herein. Computer 501 is communicatively coupled to ultrasound device 516 and motion tracking device 502 via a network interface 508, such as an Ethernet or wireless data connection, which in turn can communicate via one or more networks 504, such as the Internet or other public or private networks. According to some examples, data from ultrasound device 516 and/or motion tracking device 502 is stored persistently on a computer communicatively coupled to, and retrieved by, computer 501 via network 504. Computer 501 also includes a monitor, on which generated guidelines may be displayed. Other configurations of system 500, associated network connections, and other hardware, software, and service resources are possible.

While the foregoing disclosure has been described in some detail by way of illustration and example for purposes of clarity and understanding, it will be clear to one of ordinary skill in the art from a reading of this disclosure that various changes in form and detail can be made without departing from the true scope of the disclosure and may be practiced within the scope of the appended claims. For example, all the methods, systems, and/or component parts or other aspects thereof can be used in various combinations. All patents, patent applications, websites, other publications or documents, and the like cited herein are incorporated by reference in their entirety for all purposes to the same extent as if each individual item were specifically and individually indicated to be so incorporated by reference.

What is claimed is:

1. A method of obtaining materials science properties of soft tissue for use in a damage model for ameliorating injuries in a subject performing an assembly line manufacturing process, the method comprising:
   obtaining physical parameters characterizing a tendon of an individual under each of a plurality of loading conditions;
   fitting a soft tissue damage model based on the parameters, wherein the soft tissue damage model comprises at least two damage regimes, each of the at least two damage regimes comprising one of: a no-damage regime, a sub-rupture damage regime, or a tear propagation regime; and
   ameliorating injury in performing the manufacturing process by providing, to the subject, guidelines that restrict movement of the subject in preforming the manufacturing process based on the soft tissue damage model, wherein the guidelines based on the soft tissue damage model comprise a limitation on a number of repetitions of a movement of the tendon of the subject, wherein the subject performs the manufacturing process in accordance with the guidelines, whereby an overuse injury to the tendon of the subject is prevented, wherein the overuse injury comprises tear propagation.

2. The method of claim 1, wherein the obtaining the physical parameters comprises measuring at least one parameter of the tendon of the individual using an ultrasound device.

3. The method of claim 2, wherein the ultrasound device comprises a shear wave ultrasound device, and wherein the parameters comprise a shear modulus.

4. The method of claim 2, wherein the ultrasound device comprises a longitudinal ultrasound device, and wherein the parameters comprise at least one of a Young's modulus or a cross-sectional area of the tendon of the individual.

5. The method of claim 1, wherein the plurality of loading conditions comprise a plurality of postures of the individual.

6. The method of claim 1, wherein the plurality of loading conditions comprise a plurality of positions of the individual.

7. The method of claim 1, wherein the soft tissue damage model comprises a finite element method model.

8. The method of claim 1, wherein the tendon comprises a supraspinatus tendon.

9. The method of claim 1, wherein the soft tissue damage model is based on damage regime information comprising at least one of: ultrasound data, computerized axial tomography (CAT) scan data, magnetic resonance imaging (MRI) scan data, destructive testing data, cadaver material, animal material, polymer surrogate material, molecular dynamic modeling (MDM) data, publication data, or a combination thereof.

10. The method of claim 1, further comprising individualizing the guidelines by applying one or more demographic variables of the subject.

11. A system for obtaining materials science properties of soft tissue for use in a damage model for ameliorating injuries in a subject performing an assembly line manufacturing process, the system comprising at least one electronic processor that executes instructions to perform operations comprising:
  obtaining physical parameters characterizing a tendon of the individual under each of a plurality of loading conditions; and
  fitting a soft tissue damage model based on the parameters, wherein the soft tissue damage model comprises at least two damage regimes, each of the at least two damage regimes comprising one of: a no-damage regime, a sub-rupture damage regime, or a tear propagation regime;
  wherein guidelines are provided to the subject, wherein the guidelines restrict movement of the subject in preforming the manufacturing process based on the soft tissue damage model, wherein the guidelines based on the soft tissue damage model comprise a limitation on a number of repetitions of a movement of the tendon of the subject, wherein the subject performs the manufacturing process in accordance with the guidelines, whereby an overuse injury to the tendon of the subject is prevented, wherein the overuse injury comprises tear propagation.

12. The system of claim 11, further comprising an ultrasound device, wherein the obtaining the physical parameters comprises measuring at least one parameter of the tendon of the individual using the ultrasound device.

13. The system of claim 12, wherein the ultrasound device comprises a shear wave ultrasound device, and wherein the parameters comprise a shear modulus.

14. The system of claim 12, wherein the ultrasound device comprises a longitudinal ultrasound device, and wherein the parameters comprise at least one of a Young's modulus or a cross-sectional area of the tendon of the individual.

15. The system of claim 11, wherein the plurality of loading conditions comprise a plurality of postures of the individual.

16. The system of claim 11, wherein the plurality of loading conditions comprise a plurality of positions of the individual.

17. The system of claim 11, wherein the soft tissue damage model comprises a finite element method model.

18. The system of claim 11, wherein the tendon comprises a supraspinatus tendon.

19. The system of claim 11, wherein the soft tissue damage model is based on damage regime information comprising at least one of: ultrasound data, computerized axial tomography (CAT) scan data, magnetic resonance imaging (MRI) scan data, destructive testing data, cadaver material, animal material, polymer surrogate material, molecular dynamic modeling (MDM) data, publication data, or a combination thereof.

20. The system of claim 11, wherein the operations further comprise individualizing the guidelines by applying one or more demographic variables of the subject.

\* \* \* \* \*